United States Patent [19]

Molimar

[11] Patent Number: 4,539,845
[45] Date of Patent: Sep. 10, 1985

[54] DRIVING SYSTEM FOR EXCITING A MECHANICAL COMPONENT AT ITS RESONANT FREQUENCY FOR FATIGUE-TESTING PURPOSES

[75] Inventor: Maurice Molimar, Les Lyons, France

[73] Assignee: Renault Vehicules Industriels, Lyons, France

[21] Appl. No.: 534,028

[22] Filed: Sep. 20, 1983

[30] Foreign Application Priority Data

Sep. 23, 1982 [FR] France .................. 82 16046

[51] Int. Cl.³ .............................. G01M 7/00
[52] U.S. Cl. ...................... 73/578; 73/668; 318/127
[58] Field of Search ............. 73/577, 578, 579, 664, 73/668; 318/127, 128, 132

[56] References Cited

U.S. PATENT DOCUMENTS

| | | | |
|---|---|---|---|
| 3,864,618 | 2/1975 | Hammond | 318/807 |
| 4,002,058 | 1/1977 | Wolfinger | 73/578 |
| 4,049,997 | 9/1977 | McGhee | 73/664 |
| 4,479,098 | 10/1984 | Watson | 318/127 |

FOREIGN PATENT DOCUMENTS 1581464 2/1968 France .
427989 5/1935 United Kingdom .

*Primary Examiner*—Stephen A. Kreitman
*Attorney, Agent, or Firm*—Beveridge, DeGrandi & Weilacher

[57] ABSTRACT

Device for fatigue-testing a mechanical component by exciting this component (1), to which massive armatures (2, 3) may be attached, using an electromagnetic vibrator (13) fed by a generator, characterized in that the said generator comprises a displacement sensor (14) placed between two parts of a vibrating assembly (1, 2, 3) and generating a sinusoidal signal; a root-mean-square value converter (5) converting this alternating signal into a direct current signal of root-mean-square value; and an analog divider circuit (7) receiving the sinusoidal signal as numerator (8) and the root-mean-square value signal produced by the said converter as denominator (6), with the output signal (9) from this divider (7) being used after amplification (12) to drive the electromagnetic vibrator (13) acting on the vibrating assembly.

7 Claims, 2 Drawing Figures

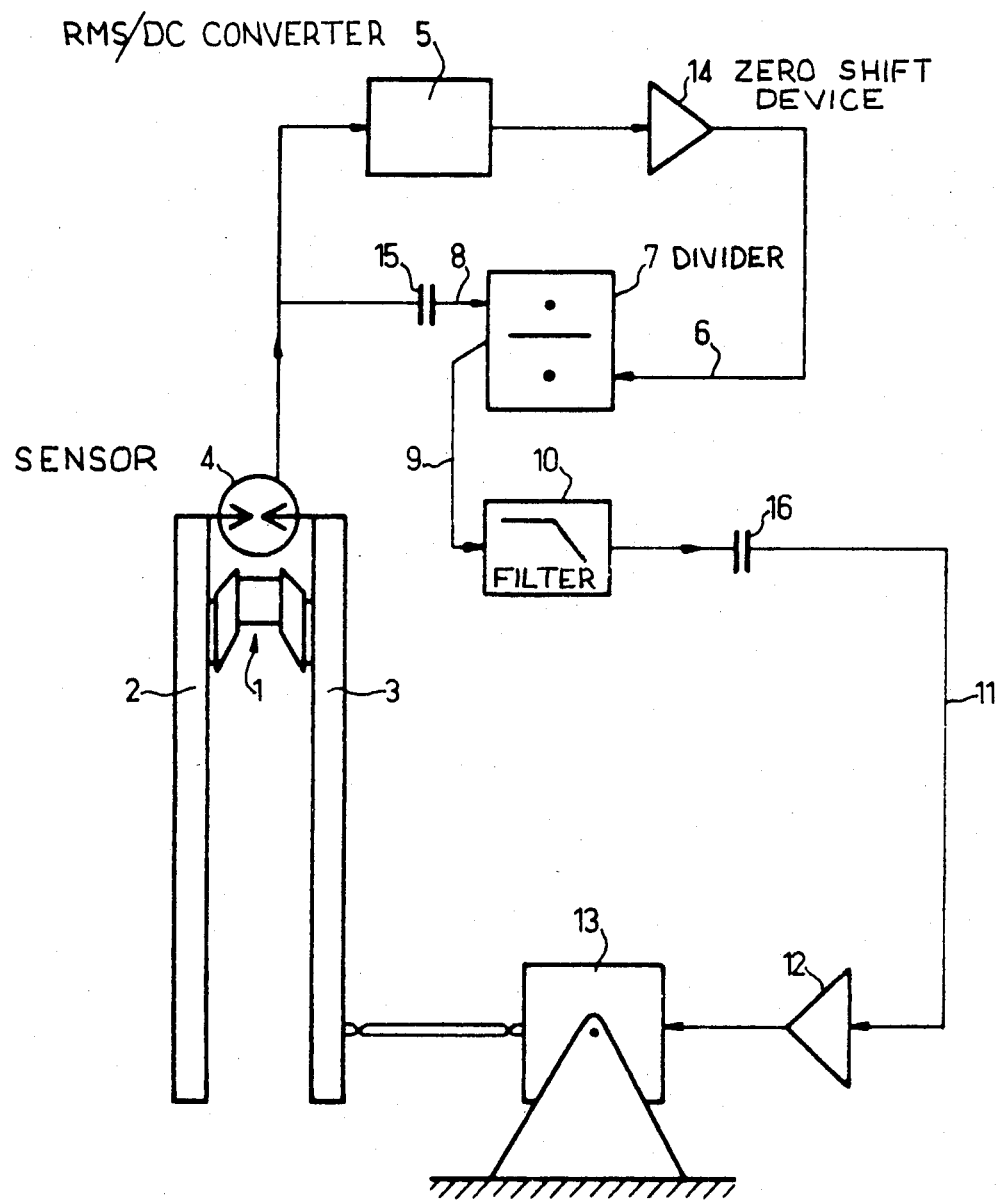

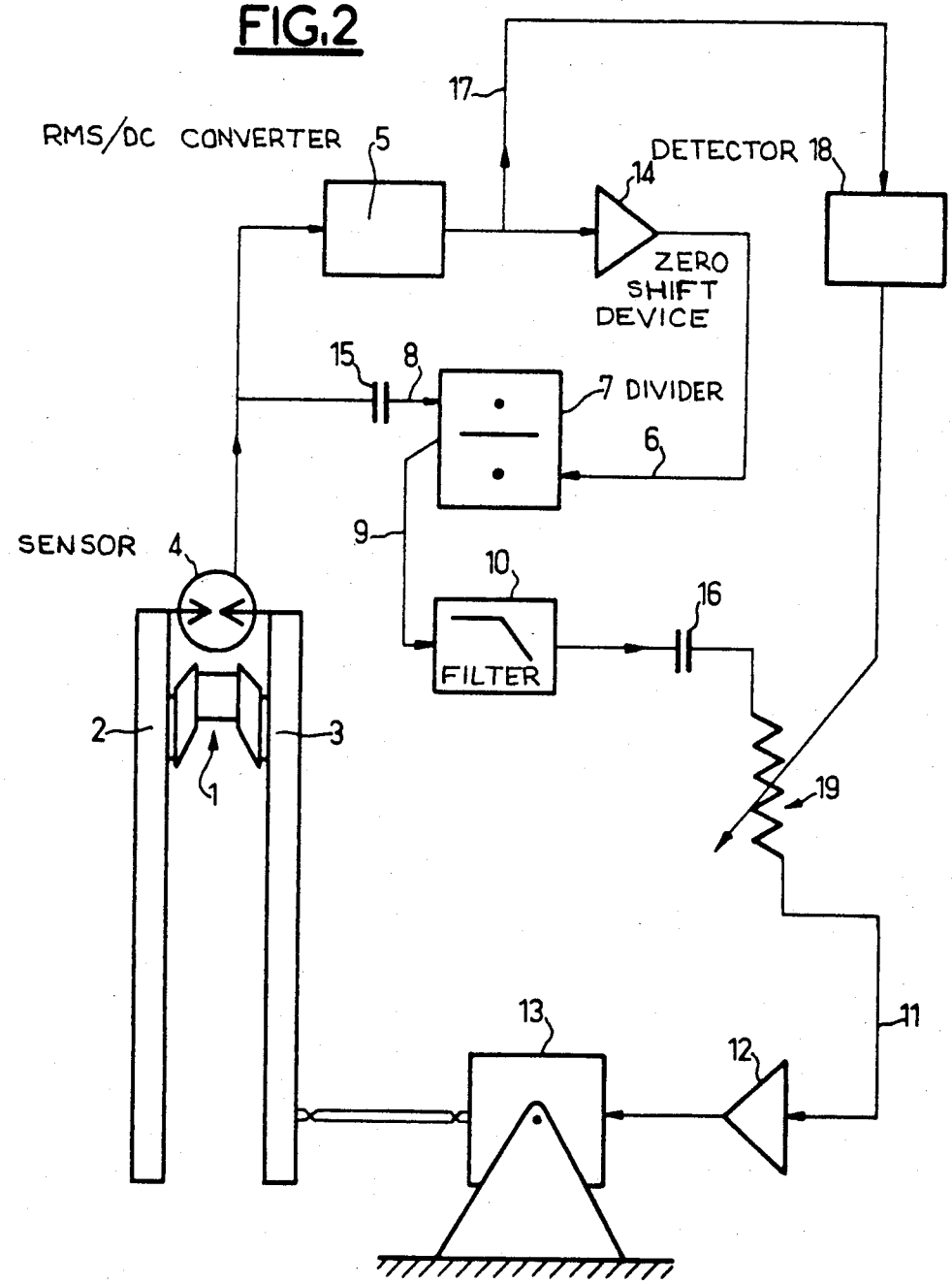

DRIVING SYSTEM FOR EXCITING A MECHANICAL COMPONENT AT ITS RESONANT FREQUENCY FOR FATIGUE-TESTING PURPOSES

BACKGROUND OF THE INVENTION

The invention relates to the fatigue testing of mechanical components, notably engine or motor components.

These fatigue tests are often carried out with mechanical machines comprising cams, excentrics, linkages, cranks and rams working at limited frequencies and requiring very rigid and heavy frames in order to apply the high forces needed.

Another solution consists in exciting the element under test at its natural frequency by an exciter or high-frequency ram, which enables the testing time and forces applied to be reduced since maintenance of the oscillations only needs the energy loss absorbed by friction and internal damping to be made up, and these are low in metals. Owing to this low damping the overtension factor at resonance is very high, which means that the exciting device only needs to supply a small force to maintain large movements corresponding to considerable stresses.

Consequently an exciter is used driven by a generator the frequency of which is tuned to that of the element under test.

In particular electromagnetic vibrators are easy to use and can reach much higher frequencies than the previous mechanical machines, but the efforts they supply are very limited so that if the natural frequency of the element under test varies due, for example, to heating, work hardening, incipient failure or any other reason, so that it differs from that of the generator, the effort required of the vibrator soon becomes too large to maintain the movement amplitudes and the stress levels. It is therefore necessary to constantly retune the generator frequency to the natural frequency of the element under test, and this constitutes a problem which has not found a satisfactory solution at the present time.

In addition, during the endurance test, it is necessary to control the electrical level of the signal so that the effective amplitude of the mechanical vibrations of the element under test are maintained at a preset value corresponding to constant deformations and stresses characteristic of the endurance test.

Consequently the aim of the invention is to solve this problem as simply and automatically as possible, i.e. to produce an electric generator with a sinusoidal frequency, the frequency of which is at all times equal to the natural frequency of the element subjected to the tests and the amplitude of which is constantly controlled, so that the natural amplitude of the mechanical vibrations of the element subjected to the tests is equal to a predetermined setpoint value.

SUMMARY OF THE INVENTION

The invention consists in using a displacement sensor which measures the deformations of the element under test and supplies a sinusoidal electric signal, and in using an analog divider circuit which receives this electric signal on its numerator input and receives on its denominator input a root-mean-square signal supplied by a root-mean-square value converter also fed with the signal from the sensor. The output from the divider circuit, after filtering and amplification as required, feeds the electromagnetic exciter acting on the element under test. This same root-mean-square value signal can be used for controlling the level of the signal feeding the exciter.

BRIEF DESCRIPTION OF THE DRAWINGS

Other features of the invention will appear from the following description of an embodiment taken as an example and shown in the appended drawings in which:

FIG. 1 shows the frequency feedback control circuit schematic;

FIG. 2 shows the complete system schematic with amplitude feedback control.

DETAILED DESCRIPTION

In the FIGS. 1 marks the element under test, 2 and 3 the armatures of the test device and 4 the displacement sensor mounted between these same armatures.

This displacement sensor 4 is of the contactless type since the bending or flexure deformations are not linear in form.

This sensor thus generates a sinusoidal electric signal having an amplitude proportional to the maximum deformation and which can be expressed as:

$$y_1 = a \sin \omega t$$

A root-mean-square/direct current converter 5 is used on the sensor 4 output to supply a continuous (d.c.) voltage proportional to the amplitude of the displacement, this root-mean-square value being in principle equal to $a/\sqrt{2}$.

This voltage is sent by 6 to the denominator of an analog divider circuit 7 the numerator of which receives the signal $y_1$ from the sensor through 8.

The output signal leaving this divider circuit 7 via 9 can therefore be expressed as:

$$y_2 = \frac{(a \sin \omega t)}{(a \sqrt{2})} = \sqrt{2} \sin \omega t$$

which is therefore a sine wave with constant amplitude of $\sqrt{2}$ and frequency of $\omega/2\pi$ which is the natural frequency of the component 1 under test.

This signal $y_2$ leaving via 9 passes through a low-pass filter 10 the functions of which are firstly to eliminate the high-frequency parasitic signals in the circuit and the residual ripple from the high-frequency carrier displacement sensor, and secondly to shift the phase of the output signal compared with the input signal by the filter transfer function in order to compensate for the phase shifts introduced by the various circuit elements.

The signal thus filtered is fed through 11 after amplification 12 to the electromagnetic exciter 13 which acts on the armature 3.

On start-up there is no sensor signal, i.e. the amplitude of the $y_1$ signal is zero. The analog divider circuit 7 is then in indetermination conditions of the 0/0 type and saturates. In order to avoid this drawback a non-zero denominator is required, which is obtained by superimposing a low direct current voltage on the root-mean-square value by means of amplifier which is operable as a zero shift device 14. This results in a slight loss of linearity, but this not troublesome provided the value thus added is low enough.

A capacitor 15 of the order of a microfared is preferably inserted between the sensor 4 and the input 8 of the divider 7 so as not to receive any d.c. component at the numerator.

Under these conditions, on start-up, i.e. with a zero root-mean-square value, the divider board behaves as a very-high-gain amplifier for the sensor signal, since the denominator is very small. So the divider 7 greatly amplifies all the input parasitics so much that these are then of a high enough level at the input to the power amplifier 12 to provide a feed to the electromagnetic vibrator 13 and excitation of the test device which will vibrate at its natural frequency. The oscillations are thus set in motion automatically.

In operation the active filter 10 is set so that the current is as low as possible at the output of the power amplifier 12 in order to correspond to the minimal effort of the vibrator corresponding to resonance. A capacitor 16 inserted on the filter output enables a symmetrical force to be applied to the vibrator by eliminating the d.c. component.

In order to provide amplitude control of the oscillations of the element under test the method used is as shown in FIG. 2 with the root-mean-square signal leaving the converter 5 being sampled via 17 and being used to control the gain of the amplifier 12 or, more simply, the level of the input to this amplifier at 11. For this purpose a detector 18, for example, is used; this comprises a minimum threshold and a maximum threshold, both defined on either side of the set setpoint value, with this detector acting when necessary in the required direction on a level adjustment potentiometer 19.

The device according to the invention is therefore relatively simple, only requires low-energy components and can be very quickly adapted to all kinds of mechanical elements like crankshafts, cylinder liners, connecting rods, flywheel fixings or others which are converted into resonating elements owing to their natural elasticity combined with the masses of the armatures 2 and 3 which are fixed to them; these latter can be adapted in masse and shape to the types of components being tested.

I claim:

1. A device for fatigue-testing a mechanical component be exciting this component (1), to which massive armatures (2, 3) may be attached, using an electromagnetic vibrator (13) fed by a generator, characterized in that the said generator comprises a displacement sensor (4) inserted between two parts of a vibrating assembly (1, 2, 3) and generating a sinusoidal signal; a root-mean-square value converter (5) converting this alternating signal into a direct current signal of root-mean-square value; and an analog divider circuit (7) receiving the sinusoidal signal as numerator (8) and the root-mean-square value signal produced by the said converter as denominator (6), with the output signal (9) from this divider (7) being used after amplification (12) to drive the electromagnetic vibrator (13) acting on the vibrating assembly.

2. The device according to claim 1, characterized in that a zero shift device (14) is inserted on the root-mean-square value converter (5) output so as to add a slight direct current component when there are no sensor vibrations on the sensor (4) so as to prevent any indeterminacy in the analog divider (7) and enable oscillations to be struck up.

3. The device according to claim 2, characterized in that it comprises a capacitor (15) inserted between the sensor (4) and the numerator (8) of the analog divider circuit (7) in order to eliminate any direct current component which may arise.

4. The device according to claim 1, characterized in that a low-pass active filter (10) is inserted on the output (9) of the divider circuit (7) and is adjusted to eliminate the parasitic high frequencies and provide a suitable phase shift.

5. The device according to claim 4, characterized in that a capacitor (16) is inserted at the output of the low-pass filter (10) to eliminate any direct current component and make the vibrations perfectly symmetrical.

6. The device according to claim 1, characterized in that the amplitude of the electric signals supplied by the amplifier (12) to the vibrator (13) is automatically adapted to maintain a constant predetermined amplitude of the mechanical vibrations of the vibrating assembly (1, 2, 3) by means of a feedback control (18, 19) using the root-mean-square value signal (17) leaving the root-mean-square value converter (5) as its input signal.

7. The device according to claim 6, characterized in that the said feedback control comprises a detector (18) with maximum and minimum thresholds defined on either side of a predetermined but adjustable setpoint value, with this detector acting when necessary and in the required correction direction on a potentiometer (19) adjusting the input level (11) of the electric signal going from the low-pass filter (10) or from its output capacitor (16) to the output amplifier (12).

* * * * *